United States Patent [19]

Novak et al.

[11] 4,155,846

[45] May 22, 1979

[54] MULTI-SEGMENTED ADSORPTION ION EXCHANGE OR GELL FILTRATION COLUMN APPARATUS AND PROCESS

[76] Inventors: Leo J. Novak, 2334 Rustic Rd., Dayton, Ohio 45406; Paul H. Bowdle, 7848 SW. 66th St., Miami, Fla. 33143

[21] Appl. No.: 843,663

[22] Filed: Oct. 19, 1977

[51] Int. Cl.² .............................................. B01A 13/08
[52] U.S. Cl. ................................ 210/31 C; 210/73 R; 210/198 C; 210/264
[58] Field of Search ............... 210/24, 30, 31 R, 31 C, 210/73 R, 201, 254, 264, 266, 275, 198 C; 55/67, 74, 179, 181, 390

[56] References Cited

U.S. PATENT DOCUMENTS

| | | | |
|---|---|---|---|
| 440,239 | 11/1890 | Cole | 210/201 X |
| 590,868 | 9/1897 | Wanner | 210/264 |
| 636,447 | 11/1899 | Paddock | 210/264 |
| 807,462 | 12/1905 | Heaton | 210/275 X |
| 3,205,166 | 9/1965 | Ludlow et al. | 210/24 |
| 3,686,117 | 8/1972 | Lauer et al. | 210/31 C |
| 3,992,175 | 11/1976 | Klementi et al. | 55/67 |
| 4,001,112 | 1/1977 | Barker et al. | 55/67 X |

*Primary Examiner*—John Adee
*Attorney, Agent, or Firm*—Folsom E. Drummond

[57] ABSTRACT

A process and apparatus for chromatic separation of components by flowing fluid in contact with material wherein the fluid flows downwardly through a column comprising a plurality of contacting chambers each of which contain material to be contacted, and wherein each of the chambers are selectively subjected to treatment by said fluid, the material preferably comprising adsorptive, gel or ion exchange substances, or the like, and filtration material for purification and as a continuous or discontinuous process.

8 Claims, 4 Drawing Figures

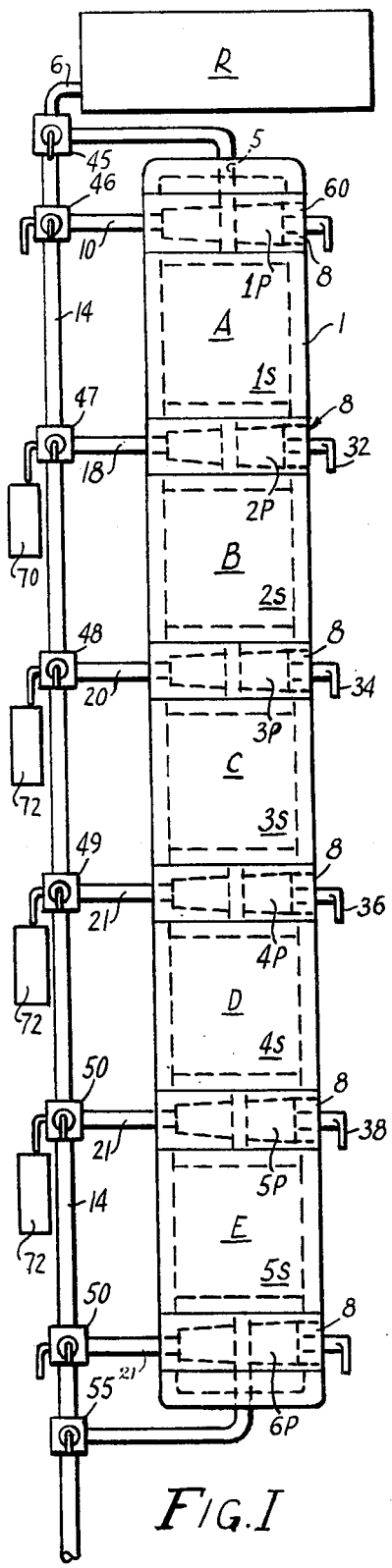
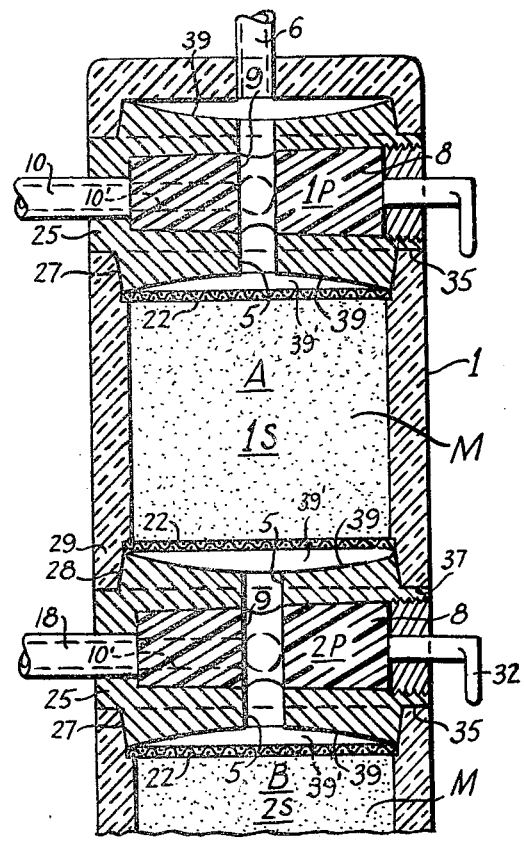
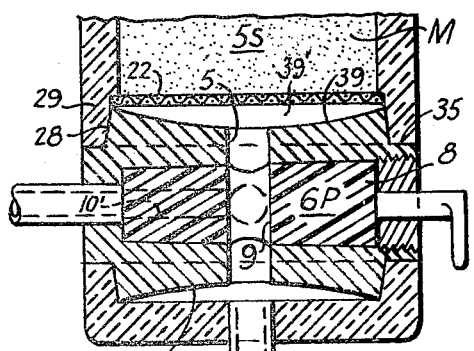
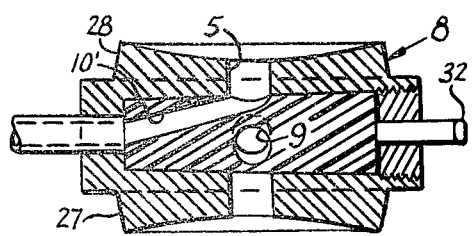
FIG. I
FIG. II
FIG. III
FIG. IV

MULTI-SEGMENTED ADSORPTION ION EXCHANGE OR GELL FILTRATION COLUMN APPARATUS AND PROCESS

BACKGROUND OF THE INVENTION

This invention relates to an improved process and apparatus for contacting fluid with material contained in a plurality of chambers within a multisegmented vertically-arranged column. Generally, the use of liquid absorptive and adsorptive ion exchange and/or gel filtration columns for the purification and treatment of various materials is known, e.g. as illustrated and described in U.S. Pat. No. 4,035,292, and patents cited therein.

The prior art patents, however, do not provide an apparatus and process for contacting fluid with material disposed in a plurality of segmented chambers of a column, and which permits fluid to flow exclusively in or out of each segment or chamber, or through all of the sequential segmented chambers containing the preselected adsorptive ion exchange or gel material and as a continuous process in accordance with the present invention.

THE INVENTION IN BRIEF

The invention, as hereinafter described and illustrated, provides an improved process and apparatus having features and advantages over the typical gel filtration and liquid/solids contacting equipment and processes involving conventional techniques.

It is a principal object of this invention to provide a novel type of multisegmented column and improved process for contacting fluids with material disposed in chambers of the segmented column to effect chemical separation and/or purification of the same. The process and apparatus is especially useful for the purification of enzymes, proteins and complex biological and macromolecular mixtures requiring separation treatment. Further, characteristic features and advantages of the invention, as well as other objects and usefulness will become readily apparent to those skilled in the art from consideration of the invention as described hereinafter and illustrated by the annexed drawing.

DRAWINGS AND DESCRIPTION

Referring to the drawings, and wherein like character references indicate like parts:

FIG. I illustrates schematically a multisegmented column having a plurality of treatment chambers arranged for selective operation in prechosen sequences by valve means and interconnecting conduits;

FIG. II depicts in detail section the construction of the chambers, screen and valve arrangement of the column, being shown partly broken away for clarity;

FIG. III depicts in detail section, likewise as in FIG. II, the lower portion of the column; and FIG. IV illustrates in detail section a three-way valve plug utilized for controlling the flow of fluid through the segmented column.

Referring to FIG. I, the multisegmented column 1 comprises a number of chambers, generally designated A, B, C, D and E which may be of the same or different size or shape. The chambers are interconnected by the valve and conduit arrangement as shown. Each of the chambers A, B, C, etc., are filled with adsorptive gel or ion exchange resin or the like treatment material, the same being generally designated M.

Eluting, extracting or concentration gradient fluid is introduced into the column 1 from a suitable receptaple or reservoir, such as indicated at R (FIG. I). Fluid flows from the reservoir into the valve controlled central passageway 5 through conduit 6. A three-way valve plug 8 disposed above and below in each chamber controls the flow of eluting fluid through the passageway 5 as well as in and out of the multisegmented column. The passageway 5 extends centrally through the column as shown best in FIGS. II and III. The three-way valve plug 8, as illustrated in more detail in FIG. IV, comprises an inner channel 9 which permits passage of eluting fluid therethrough into the central passageway 5 at one setting of the valve. Diversion of the fluid outward of the column takes place when the valve 8 is turned to connect channel 10' of the valve with passageway 5, as shown in FIG. II. Movement of the valve to a third position, whereby both channels 9 and 10' are closed, all flow of fluid is stopped from passing through the valve and thus through passageway 5 of the column.

For selectively passing elution or treating fluid into the chambers A, B, C, etc., a side conduit 14 is arranged adjacent column 1, and is selectively placed in communication with the inlet conduit 6 and passageway 5 by actuation of valve 45 as shown in FIG. I. To permit fluid to flow from or to conduit 14 and passageway 5 of column 1, valves 46, 47, 48, 49 or 50 in 14 is actuated along with the corresponding three-way valve whereby such selective flow to and from the column is achieved. Conduits e.g. 10, 18, 20 and 21 connect column 1 to the side conduit 14. Thus, utilizing the segmented column and valve arrangement in accordance with this invention, eluting fluid, or the like, treatment fluid can be made to flow exclusively and/or selectively in or out of each segment or chambers; through all of the sequential segments; through any segment from any other segment; through any or all segmented chambers containing the preselected adsorptive ion exchange or gel material as desired.

Each chamber is provided with fine mesh screens 22 which preferably are made of stainless steel. A screen is positioned on the top and bottom of each segment or chamber, as shown in FIG. II, the same being hermetically sealed abutting the three-way valve plugs. Suitable materials useful for construction of the segmental columns are, for example, polypropylene, polyethylene, polymethyl-acrylate or methacrylate, polyvinyl chloride or copolymers thereof, polycarbonate, glass, Pyrex, stainless steel, monel, Teflon and the like.

Preferred material of construction should be completely unreactive to the solvents and/or fluids to be applied therein, and transparent or translucent unless not practical. Likewise, the aforementioned screens must be made of material which is non-reactive to the substances to come in contact therewith. Screens, for example, of 200 mesh or less in size may be constructed of plastics, e.g. isotactic spun bonded polypropylene (Dupont's Typar) or Laurel Erosion plastic control cloth (Advance Construction Specialties Co. of Memphis, Tenn.). Where desired, the screens may be made of fiber glass, or metal, e.g. stainless steel, as heretofore mentioned, or other suitable material. When the chambers A, B, C, etc., are filled with gels, adsorbents, or ion exchange materials of very small size, e.g. less than the screen openings, such screens may be backed up with suitable filter paper. Whatman's No. 1 or No. 2, or equivalent, may be used for this purpose.

To provide leakproof seal construction, the bottom portion 25 of each three-way valve plug 8 of the segmented chambers, as best illustrated in FIG. II, comprises tapered, ground, smooth, fitting surfaces 27 and adjacent similarly fitting surfaces 28 of valve portion 29, the parts fitting snugly together and such as to form a fluid-proof seal. Likewise, the upper surface 35 and bottom surface 27 are ground and polished enclosing and positioning the screen 22 and papers for the screens when required. Additionally, the upper and lower surfaces 39 of the valve plug 8 are shaped to provide a small cavity 39' adjacent the screens 22 as shown in FIGS. II and III. This small cavity (e.g. 0.1 to 2 or 3 mls.) permits collection of eluting fluid around the screen surfaces so that any air bubbles will be allowed to rise and enter the central passageway 5 and so escape from the chamber. The three-way valve plugs are tapered and thus fitted to provide a fluid leakproof seal with the indented sides of the chamber as illustrated in FIGS. II and III.

The segmented column shown in FIG. I comprises five chambers A through E, as aforementioned, and includes valve actuating means 32, 34, 36 and 38 for adjusting the three-way valve plugs, designated 1P, 2P, 3P, 4P and 5P, such valve members being constructed and operated as described with respect to valve means 8 and illustrated in FIG. IV. The treatment chambers of the several segments of the column are designated 1S, 2S, 3S, 4S and 5S, for the purpose of describing the process. These chambers are filled with material M such as heretofore described and shown in FIGS. II and III.

In carrying out the process for ion exchange treatment, for example, the three-way valve connector plugs, segments, tubing connections, screens, etc., are assembled from the bottom up of the column. Referring to FIG. I, to initiate the process, the lower segment chamber 5S is inserted into the valve plug 6P with the bottom screen in place, the chamber being filled with ion exchange resin, equilibrated gel or adsorbent slurry, or the like, as required for effecting the process. The preselected fluid is then introduced through conduit line 14 through valve 45, valves 47, 48, 49 and 50 in feed line 14 being positioned to permit flow of fluid only through line 14. After admitting preselected fluid to the segment chamber 5S, drain valve 55 located near the bottom of the column is opened sufficiently to allow chamber 5S to be completely filled. Thereafter, with the top screen in place on segment chamber 5S, the preselected fluid is admitted slowly through valve 55 and to the top surface of the lower screen of 5S. Valve plug 5P is then actuated to allow the preselected fluid to flow to the top surface of its screen to eliminate all air bubbles as heretofore described. The process is repeated until the entire segmented column is assembled free of air bubbles or air pockets as well as from the associated valve, tubing and conduit lines connected to the column.

After the segmented column has been freed of air bubbles, as described, a liquid sample portion of clarified material, preferably in equilibration with the preselected fluid and concentrated form and small in volume relation to the volume of filled segmented chambers, is introduced through valve 60 at the top of the column with the bottom valve 55 just cracked open until all of the sample portion has moved past valve 60. Then equilibrating (preselected) fluid is admitted from a reservoir R and passed through valve 60 to the segment chamber or chambers, as desired, to carry out the process. After collecting a number of fractions, e.g. such as drawn out from valve 55, and with analysis showing that no additional removal of detectable impurities is removable, the eluting, extracting or concentration gradient fluid thereafter is started flowing from reservoir R and into the desired chamber or chambers of the segmented column 1.

The eluting fluid for operation of the process consists of a preselected fluid, e.g. comprising a solute containing fluid having, if desired, a concentration gradient and controlled pH molarity and composition depending upon the material being treated. During operation of the process, the eluting fluid can be passed exclusively through any particular segment chamber of the column, for example, through segment chamber 1S, by flowing the fluid through valve 60, thence through 1P, and with the three-way valve 32 open, to side arm 14 out through valve 47 to receptable means, such as indicated at 70. If, however, segment chamber 3S is to be exclusively eluted, then valve 60 is closed and valve 45 opened to allow eluting fluid to flow downwardly through side conduit 14 and then through valve 48 and conduit 20. The three-way plug valve 32 is positioned to prevent eluting fluid from passing into 2P from the side conduit 14 while plug valve 34 is positioned to permit flow of fluid from valve 48 and 3S chamber. To collect eluting fluid from 3S, plug valve 36 is positioned to allow fluid to flow outward through conduit 21 and valve 49 and be collected as at 72. Likewise, by operating the proper plug valve and side valve connected with side conduit 14, as described for eluting chamber 1S, any one or a number of the segmented chambers of the column may be placed in operation, and contacted eluting fluid collected from any chamber of the segmented column as desired.

The advantages in carrying out the eluting process in accordance with this invention are significant. To enumerate a number, for example, there is:

1. Decreased elution or extraction volumes required to attain purified moieties.

2. Higher concentration of desired solute or molecular species attained in eluate or extractive fluid. Further, the process:

3. Permits elution or extraction at preselected segment chambers of the column.

4. Permits greater insight into the absorption or adsorption differences, throughput velocity, stability, mobility, etc., of pertinent molecular species in a sample.

5. Permits reverse selective absorption and/or elution at preselected segment chambers.

6. Permits more than one type of segment chamber materials composition to be used for purification simultaneously, and also 7. Permits segment chambers of different capacity or shape to be used simultaneously, and as a continuous process.

The following examples are representative but not limitative of applications for utilizing the segmented column and process of this invention, the same being described relative to the treatment of urokinase, a thrombolytic promoter in urine, having important medical uses.

EXAMPLE 1

Comparison of Segmented Column Gel Filtration Concentration of Urokinase With "Regular" Column Technique Urokinase concentrate was prepared as per Example 4 of U.S. Pat. No. 3,755,083, of Leo J. Novak, from 1340 liters of human male pooled urine. It was concentrated with a diaflo membrane PM-10 (Amicon Corp., Cambridge, Mass.) to 10.5 ml. after cold dialytic equilibration with pH 6.5–0.1 M phosphate buffer ($NaH_2PO_4$/$Na_2HPO_4$), −0.1 M NaCl–0.1% Tris for 18 hours at 5° C.

After cold high speed centrifugation, the clear sample contained some $6.6 \times 10^6$ CTA units by the fibrin-clot-lysing-tube method and 558 mg. of $A_{280}$ protein or about 10,700 CTA/mg. $A_{280}$ activity.

A six segmented round Pyrex column having 1" diameter by 2" segments was prepared as previously described with 15 ml. volume each of equilibrated Sephadex 100 (Pharmacia Corp.) from a slurry of same in the aforementioned phosphate-NaCl-Tris buffer, equilibrated for 24 hours at 5° C.

A 5 ml. sample of this urokinase concentrate was introduced onto the top screen of the top segment chamber followed by the same $PO_4$-NaCl-Tris solution at a hydrostatic pressure of 5–6 inches. Effluent from the bottom valve of the segmented column was collected (having passed sequentially through all six chambers) with an automatic fractionator in polyethylene tubes. All at 10°–11° C. ambient temperature (cold room). Fractions were collected until the $A_{280}$ spectrophotometric reading passed through a maximum and decreased.

The bottom valve of the column was then closed and each chamber segment eluted or washed separately with the same $PO_4$-NaCl-Tris buffer solution, collecting 5 ml. fractions until the $A_{280}$ reading was less than 0.01–0.05.

Fractions from each of the six segments were pooled and assayed for urokinase and $A_{280}$ optical density. Results are shown in the following Table 1.

Table 1

Six Segmented Chambered Column Gel Filtration of Urokinase with Sephadex-100-NaCl-Tris - pH 6.5 - 0.1 M $PO_4$ Solution

| Segment No. | Pooled Volume Effluent ml. | Total mg. A280 | CTA's Total | Activity CTA's/mg. A280 Protein |
|---|---|---|---|---|
| 1 | 80 | 15 | $4 \times 10^3$ | — |
| 2 | 60 | 11 | $0.7 \times 10^6$ | 64,000 |
| 3 | 65 | 20 | $1.2 \times 10^6$ | 60,000 |
| 4 | 55 | 5 | $0.3 \times 10^6$ | 60,000 |
| 5 | 168 | 83 | $8 \times 10^3$ | — |
| 6 | 300 | 130 | $9 \times 10^3$ | — |

The Process of Example 1 was carried out using Conventional Column and Process Technique.

A 1"×8" round Pyrex column was filled with the same equilibrated Sephadex-100 to a total volume of 90 ml. and 5 ml. of the same preparation of concentrated urokinase preparation stratified thereon using generally established technique. The $PO_4$-NaCl-Tris buffer was passed therethrough collecting 5 ml. fractions.

A total of 800 ml. of eluate was collected with a main peak of activity from 500 ml. to 625 ml. and some lesser additional activity from 625 ml. to 725 ml. When pooled they gave some $1.8 \times 10^6$ CTA's, 41 mg. $A_{280}$ protein and an activity of about 44,000/$A_{280}$.

Thus, the pool of 225 ml. from regular column gel filtration gave only about 82% of the recovery from the segmented column and in a pooled volume 1.8 times that from the segmented column.

EXAMPLE 2

Pyrogen Removal Comparison Between a Five Segmented Column and a Regular Column Using IRC-50 Ion Exchange Resin for Urokinase Concentrate To two hundred gallons of pooled human male urine stored at 15° C. adjusted to pH 5.0 with cold 10% Hcl aqueous solution was added 100 gm. of Hi-SiL (a purified silica having adsorptive surfaces of 160 square meters per gram), and previously washed 4 times with 500 ml. of distilled water. After stirring for 30 minutes at room temperature the Hi-SiL Absorbate was cold centrifugally separated and dispersed in 3000 ml. of a 5° C. cold, 33% saturated solution of $(NH_4)_2SO_4$ adjusted to a pH 9.5 (added $NH_4oH$) aqueous solution in a 1 gallon polyethylene container. The resultant mixture was stirred for one hour at room temperature, cold centrifuged and the clear centrifugate made 60% saturated with $(NH_4)_2SO_4$, left standing at 10° C. for 2 hours, then cold centrifuged and the precipitate therefrom dissolved in 100 ml. of cold pyrogen free 0.02 M $Na_2HOP_4$ pH 8.0 buffer and this was twice ultrafiltered through a PSAC Pellicon membrane to a concentrated volume of 30 ml. by adding 80 ml. of said pyrogen free buffer 0.02 M $Na_2HPO_4$ at pH 8.0 which reduced the $(NH_4)_2SO_4$ to inconsequential amounts in the final concentrate. The Pellicon membranes are made by the Millipore Corp., Bedford, Mass. 01730, and the PSAC membrane passes by pressure filtration molecules whose size is in the 1000 approximate range. Thus, urokinase is concentrated while water and inorganics pass through such a membrane. The final concentrate contained $2.8–3.0 \times 10^6$ CTA's, and $A_{280}$ of 300 mg. total protein.

IRC-50 (an ion exchange resin manufactured by Rohm and Haas Co., Philadelphia, Pa.) of 200 mesh particle size range mesh was equilibrated with pyrogen free 0.02 M $Na_2PHO_4$ pH 8.0 buffer at 10° C. for 24 hours. A five segmented chamber column was utilized having each of the chambers filled with this resin. Each chamber (1"×4" dimension) contained 25–25.5 volume of resin plus interstitial fluid. The column was washed with 200 ml. of said buffer. Thereafter 30 ml. of the above urokinase concentrate was carefully stratified onto the top screen surface of the top segment chamber followed by the introduction of phosphate buffer and then collecting 60 ml. of phosphate effluent separately from each of the five segment chambers. Results on these effluents are shown in Table 2.

Table 2

Pyrogenicity Versus Urokinase Activity of Phosphate Effluents from Five Segment Chambers of a Column Containing IRC-50 Equilibrated Resin

| Segment No. | Effluent Volume ml. | Percent of Original Urokinase | U.S.P. Pyrogen Test ° C. Rise** in Temperature |
|---|---|---|---|
| 5 | 60 | 0.5 | 3.2 |
| 4 | 60 | 0.6 | 2.7 |
| 3 | 60 | 4.0 | 0.5 |
| 2 | 60 | 1.6 | 0.4 |
| 1 | 60 | 0.6 | 0.3 |

Table 2-continued
Pyrogenicity Versus Urokinase Activity of Phosphate Effluents from Five Segment Chambers of a Column Containing IRC-50 Equilibrated Resin

| Segment No. | Effluent Volume ml. | Percent of Original Urokinase | U.S.P. Pyrogen Test ° C. Rise** in Temperature |
|---|---|---|---|
| | Original Sample* | | 4.6 |

*Diluted with pyrogen free isotonic salt solution to obtain 3 ml. containing 5000 CTA's injected for each Kg. of rabbit body weight.
**1 ml. effluent plus 2 ml. of pyrogen free isotonic salt solution.

Now each segment was separately eluted with 60 ml. of 0.5 M pyrogen free salt solution containing 0.2% NH₄OH.

Each segment effluent was ultrafiltered at 10° C. and concentrated twice to 20 ml. with a PSAC membrane by adding 80 ml. of 0.16 pyrogen free salt solution. It was rediluted to 60 ml. and tested for urokinase and pyrogens. Results are shown in the following Table 3.

Table 3
Pyrogenicity Versus Extracted Urokinase Activity from a Five Unit Segmented Column Filled With Equilibrated IRC-50 Resin

| Segment No. | Volume of Effluent ml. | Percent Original Urokinase Found | U.S.P. Pyrogen Test °C.* 3 Rabbits Average |
|---|---|---|---|
| 5 | 60 | 0.5 | 1.4 |
| 4 | 60 | 0.9 | 1.5 |
| 3 | 60 | 9.2 | 0.2 |
| 2 | 60 | 45.0 | 0.4 |
| 1 | 60 | 28.0 | 0.4 |

*diluted with pyrogen free isotonic salt solution to give 5000 CTA's per 3 ml. per Kg. rabbit body weight.

The results show that the urokinase with satisfactory non degree of pyrogenicity came from the first three segments of the column, and indicate that this segmented column liquid ion exchange process requires less elution volume to recover some 82.2% of the starting urokinase than a comparable column would with the same volume of ion exchange resin.

Although the examples given are directed toward urokinase purification, it is apparent that the process as carried out with segmental column apparatus has advantages in many other application. For example, in the purification treatment of proteins, peptides, or amino acid mixtures. Also for the testing of minute volumes of eluate or extractive fluid from the side arm capillary tubes with, e.g. ninhydrin or fluorescent amine or specific reagents for particular amino acid moieties. Likewise, their presence or absence can be detected by tests made at prechosen locations without being forced to test only the effluent from a whole regular column at the bottom exit. The process similarly is applicable for the treatment of complex fatty mixtures in non-aqueous milieu, nucleic acids, steroids, plant extracts, alkaloids, enzymes, drug mixtures, toxins, antisera, vaccines and the like. Further use of the process and apparatus, of course, is not limited to aqueous systems, nor is the use of high pressure excluded since with minor modification, such as the utilization of side spring clips or screwed segment-valved plugs, high pressure throughput can be made use of for performing the process.

When deemed advantageous, desalting of a particular segmental area eluate, can be effected by directing the eluate through another segment of the same column which is filled with the appropriate gel composition or mixed bed ion exchange resin, such as Sephadex G-25 (a cross linked dextran gel filtration media made by Pharmacia Fine Chamicals, 800, Piscataway, N.J.).

The multisegmented column, of course, can have differing absorbents, gels, ion exchange resins arranged in linear or alternate sequences of the column.

Where the components of a complex mixture have different visible chromatic properties, it is a distinct advantage to view them in different segments of the column and elute some therefrom, for example, the pigments in green leaves, bacterial pigments, urochromes, etc. Furthermore, it is not intended that there be any unreasonable limitation on the number, size or shape of the segmental chambers composing the column for carrying out the process of the invention.

Although it is generally preferred to have round tubular column structure, the size and shape of a multisegmented column can be designed based on knowledge of the adsorptive, mobility, molecular size and shape of the components in a mixture to be separated or processed utilizing the multisegmented column in accordance with this invention.

We claim:

1. A process for contacting eluting fluid with particulate material to effect chromatic separation and/or purification of the same comprising the steps of causing the eluting fluid to flow through a column having a plurality of sequentially arranged segmented chambers, each chamber containing material to be contacted with eluting fluid, and wherein the material is disposed between screen members in the chambers, the flow of eluting fluid being permitted to pass through the screen members while inhibiting the passage of particulate material being contacted with eluting fluid, said eluting fluid being arranged to flow exclusively and/or selectively in or out of each of the segmented chambers.

2. The process as set forth in claim 1 wherein the process is applied to the purification of material selected from the group consisting of proteins, amino acid mixtures, enzymes, and complex biological and macromolecular mixtures requiring purification treatment.

3. The process as set out in claim 1 wherein the contacting eluting fluid contacts material disposed in a pluraltiy of segmented chambers of the column with eluting fluid being arranged to flow exclusively in or out of each segmented chambers.

4. The process of claim 3 wherein the segmented chambers contain preselected adsorptive ion exchange gel material.

5. The process of claim 1 wherein the material to be contacted comprises more than one type of segment chamber material for simultaneous and continuous treatment of the segmented chamber materials in the column.

6. The process of claim 1 wherein the product being eluted contains urokinase.

7. The process of claim 5 wherein the material of the segmented chamber comprises ion exchange resin.

8. Apparatus for contacting eluting fluid with materials which comprises a vertically arranged segmented chromatic column, a plurality of materials contacting chambers providing a multisegmented column, means comprising a valve controlled passageway extending through the column for passing said fluid to the chambers, a three-way valve plug means for controlling the flow of contacting fluid to each of said chambers, said chambers comprising screen means positioned on the top and bottom of the chambers of the multisegmented column, said valve plug means being shaped to provide a cavity adjacent said screen means for the removal of air bubbles therefrom, and means for selectively collecting fluid from each of said chambers.

* * * * *